United States Patent
Roeder

(10) Patent No.: US 10,925,711 B2
(45) Date of Patent: Feb. 23, 2021

(54) BRANCH GRAFT SYSTEM WITH ADJUSTABLE OPENINGS

(71) Applicant: COOK MEDICAL TECHNOLOGIES LLC, Bloomington, IN (US)

(72) Inventor: Blayne A. Roeder, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 219 days.

(21) Appl. No.: 15/950,405

(22) Filed: Apr. 11, 2018

(65) Prior Publication Data
US 2019/0314136 A1  Oct. 17, 2019

(51) Int. Cl.
*A61F 2/07* (2013.01)
*A61F 2/958* (2013.01)
*A61F 2/06* (2013.01)

(52) U.S. Cl.
CPC ........... *A61F 2/07* (2013.01); *A61F 2/958* (2013.01); *A61F 2002/067* (2013.01); *A61F 2220/0016* (2013.01); *A61F 2220/0025* (2013.01); *A61F 2220/0033* (2013.01); *A61F 2230/0006* (2013.01); *A61F 2230/0008* (2013.01); *A61F 2230/0013* (2013.01); *A61F 2230/0034* (2013.01); *A61F 2250/0008* (2013.01)

(58) Field of Classification Search
CPC ............ A61F 2/07–2002/077; A61F 2250/0006–0008; A61F 2/954; A61F 2250/006–0064; A61F 2250/0007; A61F 2250/0008
See application file for complete search history.

(56) References Cited

U.S. PATENT DOCUMENTS

| | | | |
|---|---|---|---|
| 6,344,056 B1 * | 2/2002 | Dehdashtian | A61F 2/07 623/1.35 |
| 7,955,374 B2 | 6/2011 | Erickson et al. | |
| 8,052,736 B2 | 11/2011 | Doig et al. | |
| 8,709,068 B2 | 4/2014 | Shalev et al. | |
| 9,572,652 B2 | 2/2017 | Cragg et al. | |

(Continued)

FOREIGN PATENT DOCUMENTS

| | | |
|---|---|---|
| WO | WO 2006/028925 A1 | 3/2006 |
| WO | WO 2014/096810 | 6/2014 |
| WO | WO 2015/183489 A1 | 12/2015 |

OTHER PUBLICATIONS

Extended European Search Report for 19168781.3 dated Jul. 23, 2019, 8 pgs.

*Primary Examiner* — Rebecca S Preston
(74) *Attorney, Agent, or Firm* — Brinks Gilson & Lione

(57) ABSTRACT

The present embodiments describe a multi-component endograft having a first endograft with first and second wall openings, a second endograft with a third wall opening, a third endograft with a fourth wall opening, where during an adjustment state the second and third endografts are independently adjustable, both vertically along a longitudinal axis and rotationally relative to the longitudinal axis, (1) while keeping the perimeter of the third wall opening primarily encompassed by the perimeter of the first wall opening and (2) while keeping the perimeter of the fourth wall opening primarily encompassed by the perimeter of the second wall opening.

17 Claims, 4 Drawing Sheets

(56) References Cited

U.S. PATENT DOCUMENTS

| | | |
|---|---|---|
| 2009/0216315 A1* | 8/2009 | Schreck .................. A61F 2/852 623/1.35 |
| 2010/0305686 A1* | 12/2010 | Cragg ....................... A61F 2/07 623/1.35 |
| 2011/0130819 A1 | 6/2011 | Cragg et al. |
| 2011/0130826 A1* | 6/2011 | Cragg ....................... A61F 2/07 623/1.15 |
| 2012/0095547 A1 | 4/2012 | Chuter |
| 2015/0057737 A1 | 2/2015 | Ondersma et al. |
| 2015/0173923 A1 | 6/2015 | Mayberry et al. |
| 2015/0209163 A1 | 7/2015 | Kelly |
| 2016/0184077 A1 | 6/2016 | Choubey et al. |
| 2016/0184078 A1 | 6/2016 | Choubey et al. |
| 2016/0278910 A1* | 9/2016 | Kelly ...................... A61F 2/852 |
| 2016/0367353 A1 | 12/2016 | Kelly |
| 2017/0014222 A1 | 1/2017 | Roeder et al. |
| 2017/0056151 A1 | 3/2017 | Eaton et al. |

\* cited by examiner

Fig. 1A
Fig. 1B
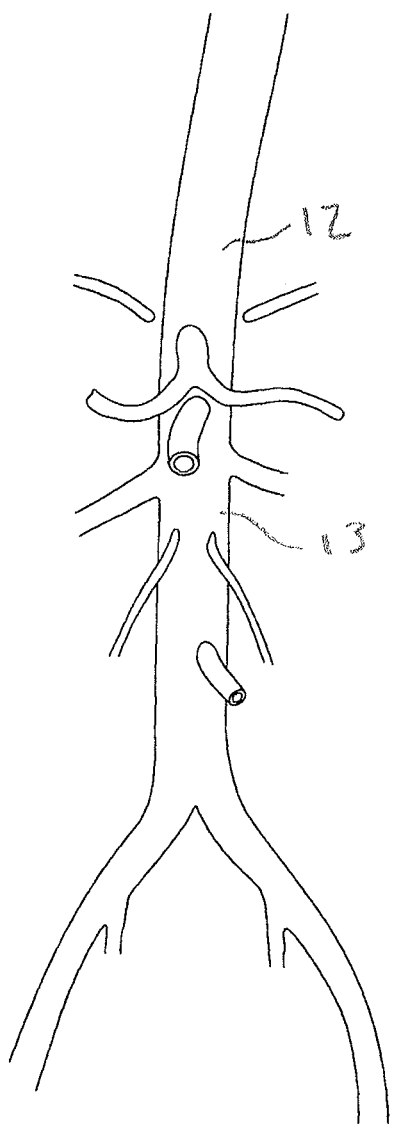
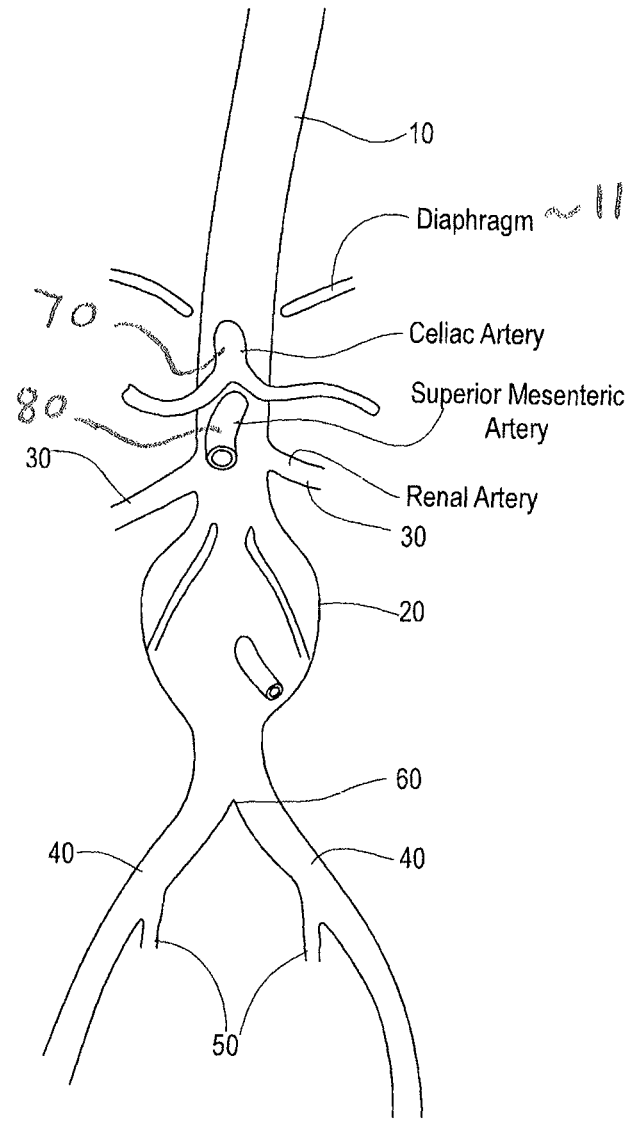

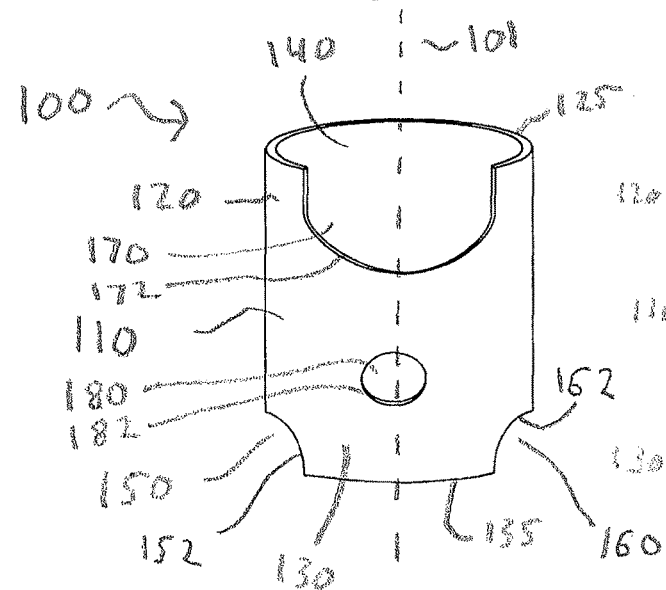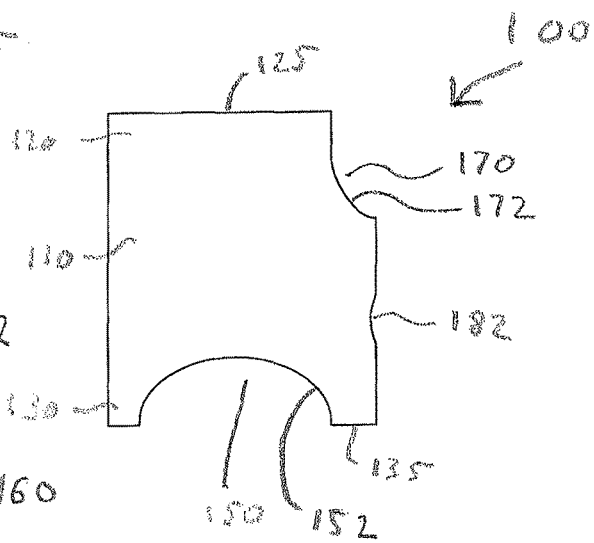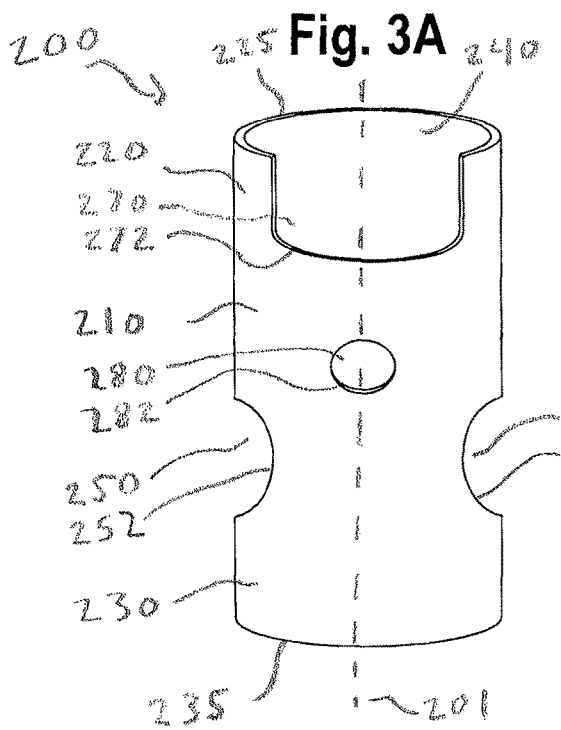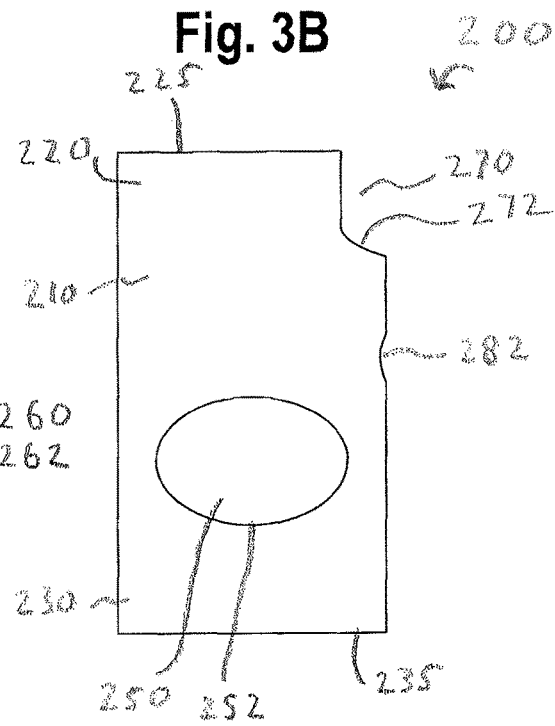

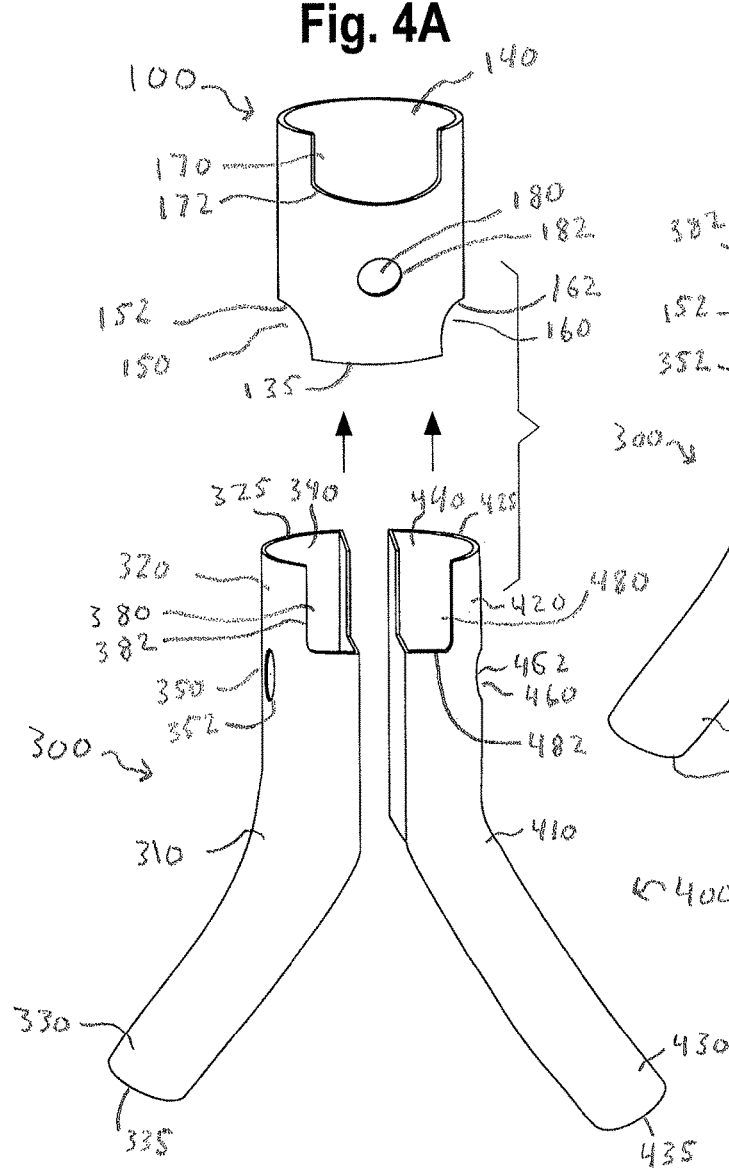
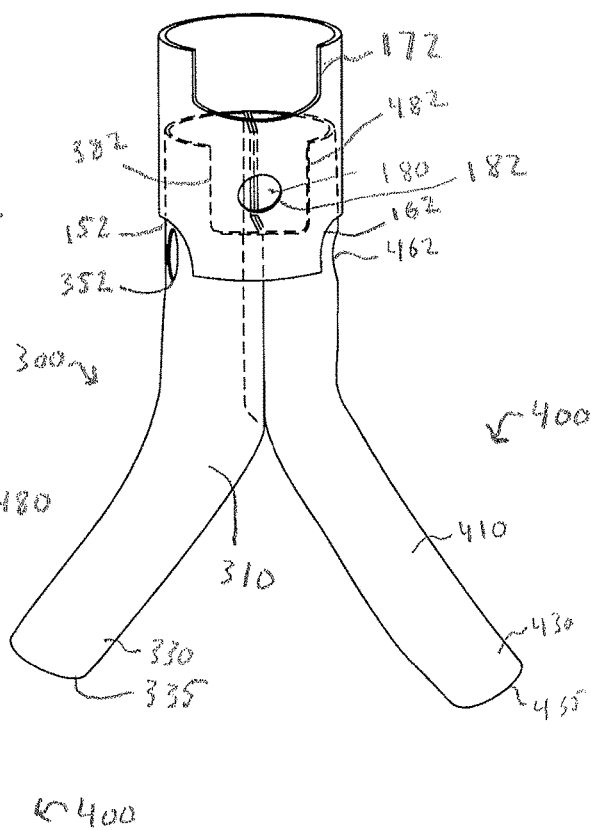

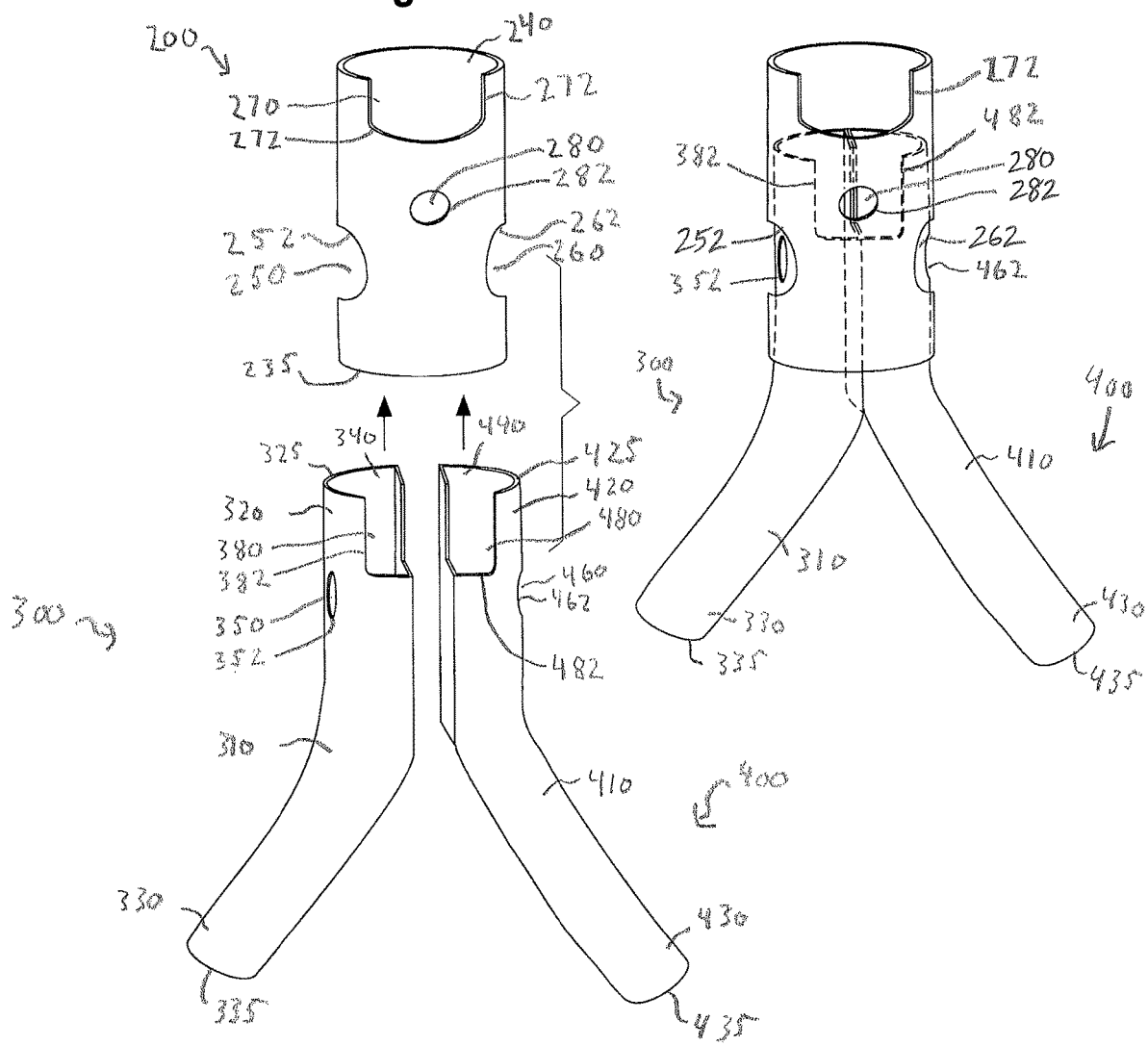

BRANCH GRAFT SYSTEM WITH ADJUSTABLE OPENINGS

BACKGROUND

The present embodiments relate generally to medical devices, and more particularly, to endografts used to treat a diseased vessel or region of vessels.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture. One study found that in Western European and Australian men who are between 60 and 75 years of age, aortic aneurysms greater than 29 mm in diameter are found in 6.9% of the population, and those greater than 40 mm are present in 1.8% of the population.

One surgical intervention for weakened, aneurysmal, or ruptured vessels involves the use of an endoluminal prosthesis such as a stent-graft or endograft. Such a prosthesis may provide some or all of the functionality of the original, healthy vessel and/or preserve any remaining vascular integrity by replacing a length of the existing vessel wall that spans the site of vessel failure. A properly placed prosthesis excludes the diseased and/or aneurysmal portion of the vessel. For weakened or aneurysmal vessels, even a small leak ("endoleak") in or around the prosthesis may lead to the pressurization of or flow in the treated vessel which may aggravate the condition that the prosthesis was intended to treat. A prosthesis of this type can treat, for example, aneurysms of the aortic arch, thoracic aorta, abdominal aortic, iliac, celiac, superior mesenteric, and/or renal arteries. When an aneurysm abuts or includes a visceral artery, the prosthesis (endograft) may incorporate these vessels so as to maintain blood flow to the relevant organ(s) and/or tissue.

In cases of aortic pathologies such as dissection or aneurysm, it is often necessary to introduce an endograft to replace or exclude the affected portion of the anatomy. Although open repair to replace a portion of the vessel may be preferable in some cases, many patients are ineligible for open surgery due to secondary issues, and require the placement of an endograft for treatment.

When an aneurysm affects a main vessel, it is important to maintain flow to the peripheral vessels. The left and right renal arteries, celiac artery, and superior mesenteric artery are peripheral vessels of the aorta. If these peripheral vessels are blocked by the main vessel prosthesis, then blood circulation is impeded, and the patient can suffer. The blockage of any peripheral vessel is usually associated with unpleasant or even life-threatening symptoms.

SUMMARY

The disclosed embodiments relate to multi-component endograft for placement in a vessel of a patient.

In one example, the multi-component endograft may include a first endograft having a first tubular main body portion. The first tubular main body portion may have a first proximal end with a first proximal opening, a first distal end with a first distal opening, and a first lumen extending therebetween along a longitudinal axis. The first endograft may also include first and second wall openings through a wall of the first tubular main body portion. The first and second wall openings may have first and second perimeters, respectively, in fluid communication with the first lumen.

The multi-component endograft may also include a second endograft having a second tubular main body portion. The second tubular main body portion may have a second proximal end with a second proximal opening, a second distal end with a second distal opening, and a second lumen extending therebetween. The second endograft may also include a third wall opening through a wall of the second tubular main body portion. The third wall opening may have a third perimeter in fluid communication with the second lumen.

The multi-component endograft may also include a third endograft having a third tubular main body portion. The third tubular main body portion may have a third proximal end with a third proximal opening, a third distal end with a third distal opening, and a third lumen extending therebetween. The third endograft may also include a fourth wall opening through a wall of the third tubular main body portion having a fourth perimeter in fluid communication with the third lumen.

The first, second, and third endografts may be constructed and dimensioned such that in an adjustment state where the second and third endografts are both within the lumen of the first endograft, the second and third endografts are independently adjustable. They may be independently adjustable both vertically along the longitudinal axis and rotationally relative to the longitudinal axis, while keeping the third perimeter of the third wall opening primarily encompassed by the first perimeter of the first wall opening and while keeping the fourth perimeter of the fourth wall opening primarily encompassed by the second perimeter of the second wall opening.

In another example, the multi-component endograft may further include a fifth wall opening through the wall of the first tubular main body portion. The fifth wall opening may have a fifth perimeter in fluid communication with the first lumen. It may further include a sixth wall opening through a wall of the second tubular main body portion. The sixth wall opening may have a sixth perimeter in fluid communication with the second lumen. It may further include a seventh wall opening through a wall of the third tubular main body portion. The seventh wall opening may have a seventh perimeter in fluid communication with the third lumen. The sixth perimeter may at least partially overlap with the seventh perimeter to form a combined perimeter. The first, second, and third endografts may be constructed and dimensioned such that in the adjustment state, the second and third endografts are independently adjustable. They may be independently adjustable both vertically along the longitudinal axis and rotationally relative to the longitudinal axis, while keeping the fifth perimeter of the fifth wall opening primarily encompassed by the combined perimeter of the sixth and seventh wall openings.

In another example, the multi-component endograft may further include an eighth wall opening through the wall of the first tubular main body portion. The eighth wall opening may have an eighth perimeter in fluid communication with the first lumen.

In another example, the third and fourth wall openings may be fenestrations. In another example, at least one of the third and fourth wall openings is a scalloped opening. In another example, the sixth and seventh wall openings are scalloped openings. In another example, the eighth wall opening is a scalloped opening or a branch. In another example, the third and fourth wall openings may be aligned with the renal arteries, the fifth wall opening may be aligned with the SMA, and/or the eighth wall opening may be aligned with the celiac artery.

In another example, the second proximal end of the second endograft fits together with the third proximal end of the third endograft to form an interference fit with a circular cross-section. In another example, the second proximal end of the second endograft and the third proximal end of the third endograft are "D" shaped or "yin-yang" shaped. In another example, at least one of the second proximal end of the second endograft or the third proximal end of the third endograft further comprises at least one hook. The hook may latch to at least one of the second or third endografts.

The methods and systems disclosed herein are nonlimiting and may be applied to other vasculature or anatomy. Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 1A and 1B are anatomical views of the aorta in a healthy and a diseased state, respectively.

FIGS. 2A-2B are front and side views of an embodiment of an endograft component.

FIGS. 3A-3B are front and side views of an alternative embodiment of an endograft component.

FIGS. 4A-4B are front views of the embodiment of FIGS. 2A-2B illustrating the insertion of leg portions.

FIGS. 5A-5B are front views of the embodiment of FIGS. 3A-3B illustrating the insertion of leg portions.

DETAILED DESCRIPTION OF THE PREFERRED EMBODIMENTS

In the present application, the term "proximal" refers to a direction that is generally upstream to the direction of blood flow during a medical procedure, while the term "distal" refers to a direction that is generally downstream to the direction of blood flow during a medical procedure.

The embodiments described below are in connection with systems and methods for the introduction and deployment of an implantable medical device in a vessel, such as endovascular prostheses, but could also be used for deploying a range of implantable medical devices including, but not limited to, stents, occlusion devices and the like.

Referring to FIG. 1, the aorta 10 is the largest artery in the human body. The diaphragm 11 separates the thoracic cavity containing the heart and lungs, from the abdominal cavity. The thoracic aorta 12 extends through the thoracic cavity and descends into the abdomen where it is referred to as the abdominal aorta 13.

Over time, the walls of the aorta 10, thoracic aorta 12, and/or abdominal aorta 13 may lose elasticity or otherwise weaken. Due to hemodynamic pressure, the vessel walls of the aorta 10 may expand in diameter, resulting in an aneurysm 20. FIGS. 1A and 1B are anatomical views of the aorta in a healthy and a diseased state, respectively. FIG. 1B illustrates an example of an abdominal aortic aneurysm 20 ("AAA"), located infra to (distal, below) the renal arteries 30 and supra to (proximal, above) the aortic bifurcation 60, external iliac arteries 40, and internal iliac arteries 50. The superior mesenteric artery 80 (SMA) is proximal to the renal arteries 30 and the celiac artery 70 is proximal to the SMA.

An aneurysm 20 can increase the risk of a possibly fatal vessel rupture if the aneurysm expands and/or bursts. A common treatment for the aneurysm is to relieve the pressure on the aneurysm by redirecting blood flow through a stent graft or endograft.

Endografts may be implanted in the aorta 10, such that blood flowing past the aneurysm 20 flows through the endograft. Use of endograft reduces pressure on the aneurysm 20 and can cause the aneurysm 20 to shrink in size. Endografts may incorporate self-expanding stents, balloon-expandable stents, and/or other support structures. The final shape, size, and position of the endograft in situ may also be modified through use of a balloon catheter.

Endografts may be implanted in other arteries (not shown). For example, the renal arteries are not often aneurysmal, but may nonetheless be treated with covered stents in cases where there is insufficient healthy vessel length to use for sealing.

Aneurysms can be classified by anatomical location. For example, a pararenal abdominal aortic aneurysm (PARA) is defined as aneurysms that have no normal aorta between the upper extent of the aneurysm and the renal arteries. It can be classified into juxtarenal (JAAA) or suprarenal (SRAAA) types. JAAA includes aneurysms that extend to just below the renal arteries without involving the renal arteries, whereas a suprarenal AAA includes that which involves at least one renal artery orifice. The aneurysm 20 shown in FIG. 1B is an example of a juxtarenal abdominal aortic aneurysm (JAAA), classified as such because the proximal extent of the aneurysm 10 is next to the origin of the renal arteries 30 without involving them.

Another category is referred to as thoracoabdominal aortic aneurysms (TAAA) which result from the continuous dilation of the descending thoracic aorta 12 extending into the abdominal aorta 13. Multiple configurations can occur anywhere along the continuum from the origin of the left subclavian artery (not shown) to the aortoiliac bifurcation 60. Type I involves most of the descending thoracic aorta 12 from the origin of the left subclavian to the suprarenal abdominal aorta. Type II is the most extensive, extending from the subclavian to the aortoiliac bifurcation. Type III involves the distal thoracic aorta to the aortoiliac bifurcation. Type IV TAAAs are limited to the abdominal aorta below the diaphragm. Type V TAAAs extend from the distal thoracic aorta including the celiac and superior mesenteric origins but not the renal arteries.

Thus, aneurysms can be located in a variety of anatomical locations and span a variety of lengths involving important branch vessels. Anatomy can also vary between patients. FIGS. 2-5 illustrate examples of multi-component endografts designed to accommodate and treat a variety of aneurysm classifications and patient anatomies.

FIGS. 2A-2B illustrate front and side views of an embodiment of a first endograft 100 that is a component of a multi-endograft system. The first endograft 100 may include a first tubular main body portion 110 having a first proximal end 120 with a first proximal opening 125, a first distal end 130 with a first distal opening 135, and a first lumen 140 extending therebetween along a central longitudinal axis 101. The first endograft 100 may have first and second wall openings 150 and 160, respectively, through a wall of the first tubular main body portion 110. The first and second wall openings 150 and 160 may each have first and second perimeters 152 and 162, respectively, both in fluid communication with the first lumen 140. The first and second wall openings 150 and 160 may be configured to align with the renal arteries 30 in a deployed state. The first endograft 100 may further include a celiac opening 170 having a celiac opening perimeter 172. The first endograft 100 may further include a first SMA opening 180 having a first SMA opening perimeter 182.

FIGS. 3A-3B illustrate front and side views of an embodiment of a first endograft 200 that is a component of a multi-endograft system. The first endograft 200 may include a first tubular main body portion 210 having a first proximal end 220 with a first proximal opening 225, a first distal end 230 with a first distal opening 235, and a first lumen 240 extending therebetween along a central longitudinal axis 201. The first endograft 200 may have first and second wall openings 250 and 260, respectively, through a wall of the first tubular main body portion 210. The first and second wall openings 250 and 260 may each have first and second perimeters 252 and 262, respectively, both in fluid communication with the first lumen 240. The first and second wall openings 250 and 260 may be configured to align with the renal arteries 30 in a deployed state. The first endograft 200 may further include a celiac opening 270 having a celiac opening perimeter 272. The first endograft 200 may further include a first SMA opening 280 having a first SMA opening perimeter 282

FIGS. 4A-4B illustrate front views of the embodiment of FIGS. 2A-2B before and after the insertion of second and third endografts 300 and 400, respectively, which may also be referred to as "legs" or "leg endografts." The second endograft 300 may have a second tubular main body portion 310 having a second proximal end 320 with a second proximal opening 325, a second distal end 330 with a second distal opening 335, and a second lumen 340 extending therebetween. The second tubular main body portion 310 may be straight or curved (as shown), for example to ease access to an external iliac artery 40. The second endograft 300 may further include a third wall opening 350 through a wall of the second tubular main body portion 310. The third wall opening 350 may have a third. perimeter 352 in fluid communication with the second lumen 340. The third wall opening 350 may be configured to align with one of the renal arteries 30 in a deployed state. The second endograft 300 may further include a second SMA opening 380 having a second SMA opening perimeter 382.

The third endograft 400 may have a third tubular main body portion 410 having a third proximal end 420 with a third proximal opening 425, a third distal end 430 with a third distal opening 435, and a third lumen 440 extending therebetween. The third tubular main body portion 410 may be straight or curved (as shown), for example to ease access to an external iliac artery 40. The third endograft 400 may further include a fourth wall opening 460 through a wall of the second tubular main body portion 410. The fourth wall opening 460 may have a fourth perimeter 462 in fluid communication with the third. lumen 440. The fourth wall opening 460 may be configured to align with one of the renal arteries 30 in a deployed state. The third endograft 400 may further include a third SMA opening 480 having a third SMA opening perimeter 482.

FIGS. 5A-5B illustrate front views of the embodiment of FIGS. 3A-3B before and after the insertion of second and third endografts 300 and 400, respectively, as described above with respect to FIGS. 4A-4B.

For the description below, first endograft 100 and first endograft 200 can generally be used interchangeably, and thus will be referred to as "endograft 100/200" or "first lumen 140/240" etc. Any differences will be called out separately.

The cross-section of the first endograft 100/200 may be generally circular. The first endograft 100/200 may seal within the thoracoabdominal aorta at any of a variety of anatomical locations, depending on the location of the aneurysm. In general, the celiac opening 170/270 will align with the celiac artery 70, the SMA opening 180/280 will align with the SMA artery 80, and the first, second, third and fourth openings (150, 160, 350 and 460) will align with the renal arteries 30.

The cross-section of the proximal ends 320 and 420 of the second and third endografts 300 and 400, respectively, may be "D-shaped" such that the flat portions are adjacent to one another so as to form a combined circular cross-section. This may also form a side-to-side seal along the flat portions and an interference fit in the expanded state. The "D-shape" including the flat portion may have a degree of flexibility such that each can move independently vertically and/or rotationally without compromising the seal. For example, circumferential rotation may be possible by the circumferential flexibility associated with a material of the selected endografts. If the flat sides of the "D-shape" are along the 12 o'clock to 6 o'clock line, and the third and fourth openings 350 and 460 are at 3 o'clock and 9 o'clock, then the third and fourth openings 350 and 460 may accommodate renal arteries 30 positioned from 2-4 o'clock and 8-10 o'clock, respectively, by having different levels of compression of the endografts. Thus, the multi-component endograft may accommodate at least two degrees of freedom relative to the location of the renal arteries 30.

Endografts 100/200, 300, and 400 may have one or more hooks (not shown) that latch onto an adjacent endograft to prevent component separation once a final configuration is achieved. The distal ends 330 and 430 may seal distally within the iliac arteries 40 or may be extended with branch stent grafts to extend through another tubular component that seals within the iliac arteries 40. In another example (not shown), instead of having "D-shaped" cross-sections, the proximal ends 320 and 420 may have a "yin-yang," shape where two curved surfaces mate to form an interference fit and side-to-side seal.

In use, the second and third endografts 300 and 400 are constructed and dimensioned to fit within the lumen 140/240 of the first endograft 100 during insertion. They may be inserted simultaneously or in sequence. Endografts 100/200, 300, and 400 may be stent grafts or another expandable endograft. Endografts 300 and/or 400 may be in a compressed state during insertion, then expand to an expanded state within the lumen 140/240 of the first endograft 100/200. The expansion of the endografts 300 and 400 may occur simultaneously or sequentially, and upon deployment the endografts 300 and 400 may be oversized within the lumen 140/240 of the first endograft 100.

At or near a target site, the endografts 300 and 400 may be adjusted independently in an adjustment state. The adjustment of endografts 300 and 400 may occur in any state of deployment, including but not limited to a partially expanded state.

Endografts 300 and 400 may be constructed and dimensioned such that in the adjustment state both are within the lumen 140/240 of the first endograft 100/200. The second and third endografts 300 and 40 may be independently adjustable along at least two degrees of freedom. First, both may be independently adjustable vertically along the longitudinal axis 101/201. Second, both may be independently adjustable rotationally relative to the longitudinal axis 101/201. This means that second and third endografts 300 and 400 may not necessarily rotate around the longitudinal axis 101/201, but will each rotate about separate axes that are offset from but generally parallel to axis 101/201. Each of endografts 100/200, 300, and 400 may have their own axis of rotation. The endografts 300 and 400 may rotate to agree in their fully expanded states.

During alignment, the third wall opening 350 may align with the first wall opening 150/250, and the fourth wall opening 460 may align with the second wall opening 160/260. The cross-sectional area of the first wall opening 150/250 may be greater than the cross-sectional area of the third wall opening 350, and the cross-sectional area of the second wall opening 160/260 may be greater than the cross-sectional area of the fourth wall opening 460. Thus, during alignment, endografts 300 and 400 may be independently adjustable vertically and rotationally (as described above) while keeping the third perimeter 352 of the third wall opening 350 primarily encompassed by the first perimeter 152/252 of the first wall opening 150/250 and while keeping the fourth perimeter 462 of the fourth wall opening 460 primarily encompassed by the second perimeter 162/262 of the second wall opening 160/260.

In one example, "primarily encompassed" may refer to having a surface area disposed within at least 50% of a perimeter of a surrounding structure. In other examples, the degree of being encompassed may be significantly greater than 50%, such as at least 60%, 70%, 80%, 90% or 100%, the latter of which refers to a boundary being fully encompassed by the perimeter of the surrounding structure.

For example, with reference to FIG. 5B, the third perimeter 352 of the third wall opening 350 is shown in this non-limiting depiction as being 100% bounded by the first perimeter 252 of the first wall opening 250. If the third perimeter 352 were adjusted a few millimeters in any direction, the surface area of the third perimeter 352 may still be entirely bounded by the first perimeter 252, or alternatively may slightly overlap with (or extend outside of) the first perimeter 252, in the latter case of which it may then be about 50 to 99% bounded by the first perimeter 252, still being primarily encompassed by the first perimeter 252 in either case.

Similarly, with reference to FIG. 4B, the third perimeter 352 of the third wall opening 350 is shown in this non-limiting depiction as being approximately 100% bounded by the first perimeter 152 of the first wall opening 150, in the sense that lower and upper edges of the third perimeter 352 are positioned vertically within lower and upper terminal boundaries formed by the scalloped shape of the first perimeter 152, and the first perimeter 152 extends around the lateral sides of the third perimeter 352. However, if the third perimeter 352 were adjusted a few millimeters in any direction, the surface area of the third perimeter 352 may still be approximately 100% bounded by the first perimeter 152, or it may slightly overlap with (or extend outside of) the first perimeter 152, and therefore may be about 50 to 99% bounded by the first perimeter 152, still being primarily encompassed by the first perimeter 152 in either case.

Furthermore, during alignment, the first SMA opening 180/280 (e.g., a fifth wall opening) of the first endograft 100/200 may align with the second SMA opening 380 (e.g., a sixth wall opening) of the second endograft 300 and the third SMA opening 480 (e.g., a seventh wall opening) of the third endograft 400. All of these SMA openings may align with the SMA 80. The second SMA opening perimeter 382 may at least partially overlap with the third SMA opening perimeter 482 to form a combined perimeter that is sealed. The combined perimeter (382 and 482) may have a cross-sectional area greater than the cross-sectional area of the first SMA opening 180/280. Thus, during alignment, endografts 300 and 400 may be independently adjustable vertically and rotationally (as described above) while keeping the first SMA opening perimeter 182/282 primarily encompassed by the combined perimeter of the second and third SMA openings 382 and 482.

Similarly, during alignment, the celiac opening 170/270 (e.g., an eighth wall opening) may align with the celiac artery 70. The celiac wall opening 170/270 may have a cross-sectional area greater than the cross-sectional area of the celiac artery 70. Thus, during alignment, all three endografts 100/200, 300, and 400 may be adjusted vertically and/or rotationally while keeping the perimeter of the celiac artery 70 primarily encompassed by the celiac opening perimeter 172/272.

The openings in the multi-component endograft may have a variety of shapes and configurations. For example, the first and second openings 150 and 160 may be scalloped openings in the sidewall that extend to the distal opening 135 of the first endograft 100, whereas the first and second openings 250 and 260 may be fenestrations made entirely within the sidewall of the main tubular body 210. The third and fourth wall openings 350 and 460, respectively, may also be fenestrations made entirely within the sidewall of the main tubular bodies 310 and 410, respectively. The celiac opening 170/270 may be a scalloped opening that extends to the proximal opening 125/225. The first SMA opening 180/280 may be a fenestration. The second and third SMA openings 380 and 480, respectively, may be scalloped openings that extend to the proximal openings 325 and 425, respectively. In other examples (not shown), any of these openings could be substituted for another type of opening, including a fenestration, scalloped openings (including rounded scallops and angled scallops), and/or a connected branch. For example, the celiac opening 170/270 and/or SMA opening 180/280 may be a connected branch configured to extend into the celiac artery or SMA, respectively.

During alignment, generally the first step may be to align the SMA opening 180/280 with the SMA artery 80. Once in place, the celiac opening 170/270 should be large enough to provide access to the celiac artery 70. Then the third opening 350 of the second endograft 300 may be aligned with the first opening 150/250 of the first endograft and further aligned with the renal artery 30. Likewise, the fourth opening 460 of the third endograft 400 may be aligned with the second opening 160/260 of the first endograft and further aligned with the opposite renal artery 30. Hence, the third opening 350 and fourth opening 460 may face in generally opposite directions (generally 180 degrees apart) relative to one another. The second and third endografts 300 and 400 may be independently adjusted vertically and rotationally. Once all relevant branch arteries are accessible, then the components may be expanded into a final configuration and held in place via an interference fit and/or hooks.

In another example, the celiac opening 170/270 may be omitted in embodiments where there is enough healthy vessel to "land" the proximal opening 125/225 distal to the celiac artery 70.

The multi-component endograft described herein has multiple advantages over existing endografts. The independent vertical and rotational adjustability is advantageous because it allows the multi-component endograft structure to accommodate a variety of aneurysm locations and patient anatomies. The legs (second and third endografts 300 and 400) are independently adjustable in the vertical direction, meaning a single off-the-shelf system can be elongated or shortened depending on the aneurysm location and patient anatomy, all while maintaining fluid flow to the celiac, SMA, and renal arteries. If one renal artery 30 is higher (supra) than the other, the legs are independently adjustable. The larger first and second openings 150 and 160 allow a large access window for the openings (fenestrations) 350 and 460 in the legs. This "one size fits all" repair device provides a physician with flexibility during the repair procedure. It can be challenging to manage all of these vessels while deploying a single endograft. As described above, this multi-component endograft system allows the physician to address one or two vessels at a time, simplifying the implant. It can also provide cost savings since one "off-the-shelf" device can be used in a wide variety of patients and anatomies. This may help reduce more costly custom implants.

The concepts described herein can be modified to accommodate a variety of aneurysm types too. The following non-limiting examples illustrate how the multi-endograft system described above and shown in the figures can be modified to address a variety of aneurysms types (see classifications described above).

For JAAAs and PRAAAs, the celiac opening 170/270 may be scalloped, the SMA opening 180/280 may be a fenestration, and the first and second openings 150 and 160 may be fenestrations (large) to accommodate a range of locations for the renal arteries 30. For PRAAAs and Type IV TAAAs, the design may also substitute a branch at the celiac opening 170/270. For Type I, II, III, and V TAAAs, the celiac opening 170/270 may be a branch, the SMA opening 180/280 may be a branch, and the first and second openings 150 and 160 may be scalloped openings.

The openings described herein may be of a variety of sizes. During alignment as described above, a general theme is that a small opening is aligned with a larger opening such that it is adjustable both vertically and rotationally without straying outside of the larger opening. While this is generally the case, it is not necessarily so. For example, the third and fourth openings 350 and 460, respectively, illustrated in FIGS. 4A-4B appear to extend slightly below the distal opening 135, thus straying outside of the perimeter of first and second openings 150 and 160. This is just one of a variety of configurations that are disclosed herein. In another example (not shown), the third and fourth openings 350 and 460, respectively, may be small and fit entirely within the perimeter of the first and second openings 150 and 160.

The embodiments described herein provide non-limiting examples of endografts that are suitable for treating an array of medical conditions, and may be especially suited for treating an aortic aneurysm. Various additional modular components may be provided for the endografts 100/200.

While references to treatment of an aortic aneurysm at or near the renal arteries may be explained as one example, it will be appreciated that endografts 100/200 can be positioned at other bodily locations to treat aneurysms or other conditions, using the system and methods described herein. The concepts and principles described herein should not be limited to the celiac, SMA, and renal arteries While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:
1. A multi-component endograft, comprising:
a first endograft comprising,
  a first tubular main body portion having a first proximal end with a first proximal opening, a first distal end with a first distal opening, and a first lumen extending therebetween along a longitudinal axis,
  first and second wall openings through a wall of the first tubular main body portion and having first and second perimeters, respectively, in fluid communication with the first lumen;
a second endograft comprising,
  a second tubular main body portion having a second proximal end with a second proximal opening, a second distal end with a second distal opening, and a second lumen extending therebetween,
  a third wall opening through a wall of the second tubular main body portion having a third perimeter in fluid communication with the second lumen;
a third endograft comprising,
  a third tubular main body portion having a third proximal end with a third proximal opening, a third distal end with a third distal opening, and a third lumen extending therebetween,
  a fourth wall opening through a wall of the third tubular main body portion having a fourth perimeter in fluid communication with the third lumen;
wherein the first, second, and third endografts are constructed and dimensioned such that in an adjustment state where the second and third endografts are both within the lumen of the first endograft, the second and third endografts are independently adjustable, both vertically along the longitudinal axis and rotationally relative to the longitudinal axis, while keeping the third perimeter of the third wall opening primarily encompassed by the first perimeter of the first wall opening and while keeping the fourth perimeter of the fourth wall opening primarily encompassed by the second perimeter of the second wall opening, and
wherein the second proximal end of the second tubular main body portion extends proximally past the first wall opening in the first endograft in a deployed state, and the third proximal end of the third tubular main body portion extends proximally past the second wall opening in the first endograft in the deployed state;
a fifth wall opening through the wall of the first tubular main body portion and having a fifth perimeter in fluid communication with the first lumen;
a sixth wall opening through the wall of the second tubular main body portion having a sixth perimeter in fluid communication with the second lumen;
a seventh wall opening through the wall of the third tubular main body portion having a seventh perimeter in fluid communication with the third lumen;
wherein the sixth perimeter at least partially overlaps with the seventh perimeter to form a combined perimeter, and
wherein the first, second, and third endografts are constructed and dimensioned such that in the adjustment state, the second and third endografts are independently adjustable, both vertically along the longitudinal axis and rotationally relative to the longitudinal axis, while keeping the fifth perimeter of the fifth wall opening primarily encompassed by the combined perimeter of the sixth and seventh wall openings.

2. The multi-component endograft of claim 1, further comprising an eighth wall opening through the wall of the first tubular main body portion and having an eighth perimeter in fluid communication with the first lumen.

3. The multi-component endograft of claim 2, wherein the eighth wall opening is a scalloped opening.

4. The multi-component endograft of claim 2, wherein the eighth wall opening is proximal to the fifth wall opening.

5. The multi-component endograft of claim 1, wherein the third and fourth wall openings are fenestrations.

6. The multi-component endograft of claim 1, wherein at least one of the third and fourth wall openings is a scalloped opening.

7. The multi-component endograft of claim 1, wherein the sixth and seventh wall openings are scalloped openings.

8. The multi-component endograft of claim 1, wherein the third and fourth wall openings face in opposite directions relative to one another.

9. The multi-component endograft of claim 1, wherein the fifth wall opening is proximal to the third and fourth wall openings.

10. The multi-component endograft of claim 1, wherein the second proximal end of the second endograft fits together with the third proximal end of the third endograft to form an interference fit with a circular cross-section.

11. The multi-component endograft of claim 1, wherein the second proximal end of the second endograft and the third proximal end of the third endograft are "D" shaped.

12. The multi-component endograft of claim 1, wherein the second proximal end of the second endograft and the third proximal end of the third endograft are "yin-yang" shaped.

13. The multi-component endograft of claim 1, wherein at least one of the second proximal end of the second endograft or the third proximal end of the third endograft further comprises at least one hook.

14. The multi-component endograft of claim 13, wherein the at least one hook latches to the first endograft.

15. The multi-component endograft of claim 13, wherein the at least one hook latches to at least one of the second or third endografts.

16. A multi-component endograft, comprising:
a first endograft comprising,
  a first tubular main body portion having a first proximal end with a first proximal opening, a first distal end with a first distal opening, and a first lumen extending therebetween along a longitudinal axis,
  first and second wall openings through a wall of the first tubular main body portion and having first and second perimeters, respectively, in fluid communication with the first lumen;
a second endograft comprising,
  a second tubular main body portion having a second proximal end with a second proximal opening, a second distal end with a second distal opening, and a second lumen extending therebetween,
  a third wall opening through a wall of the second tubular main body portion having a third perimeter in fluid communication with the second lumen;
a third endograft comprising,
  a third tubular main body portion having a third proximal end with a third proximal opening, a third distal end with a third distal opening, and a third lumen extending therebetween,
  a fourth wall opening through a wall of the third tubular main body portion having a fourth perimeter in fluid communication with the third lumen;
wherein the first, second, and third endografts are constructed and dimensioned such that in an adjustment state where the second and third endografts are both within the lumen of the first endograft, the second and third endografts are independently adjustable, both vertically along the longitudinal axis and rotationally relative to the longitudinal axis, while keeping the third perimeter of the third wall opening primarily encompassed by the first perimeter of the first wall opening and while keeping the fourth perimeter of the fourth wall opening primarily encompassed by the second perimeter of the second wall opening, and
wherein the second proximal end of the second tubular main body portion extends proximally past the first wall opening in the first endograft in a deployed state, and the third proximal end of the third tubular main body portion extends proximally past the second wall opening in the first endograft in the deployed state,
wherein at least one of the third and fourth wall openings is a scalloped opening.

17. A multi-component endograft, comprising:
a first endograft comprising,
  a first tubular main body portion having a first proximal end with a first proximal opening, a first distal end with a first distal opening, and a first lumen extending therebetween along a longitudinal axis,
  first and second wall openings through a wall of the first tubular main body portion and having first and second perimeters, respectively, in fluid communication with the first lumen;
a second endograft comprising,
  a second tubular main body portion having a second proximal end with a second proximal opening, a second distal end with a second distal opening, and a second lumen extending therebetween,
  a third wall opening through a wall of the second tubular main body portion having a third perimeter in fluid communication with the second lumen;
a third endograft comprising,
  a third tubular main body portion having a third proximal end with a third proximal opening, a third distal end with a third distal opening, and a third lumen extending therebetween,
  a fourth wall opening through a wall of the third tubular main body portion having a fourth perimeter in fluid communication with the third lumen;
wherein the first, second, and third endografts are constructed and dimensioned such that in an adjustment state where the second and third endografts are both within the lumen of the first endograft, the second and third endografts are independently adjustable, both vertically along the longitudinal axis and rotationally relative to the longitudinal axis, while keeping the third perimeter of the third wall opening primarily encompassed by the first perimeter of the first wall opening and while keeping the fourth perimeter of the fourth wall opening primarily encompassed by the second perimeter of the second wall opening, and
wherein the second proximal end of the second tubular main body portion extends proximally past the first wall opening in the first endograft in a deployed state, and the third proximal end of the third tubular main body portion extends proximally past the second wall opening in the first endograft in the deployed state; and
a fifth wall opening through the wall of the first tubular main body portion and having a fifth perimeter in fluid communication with the first lumen, wherein at least one of the second proximal end of the second tubular main body portion or the third proximal end of the third tubular main body portion extends proximally past the fifth wall opening in the first endograft in the deployed state.

* * * * *